United States Patent [19]

Mimura et al.

[11] Patent Number: 5,100,622
[45] Date of Patent: Mar. 31, 1992

[54] AUTOMATIC ANALYZING APPARATUS AND METHOD FOR CLINICAL EXAMINATION

[75] Inventors: Tomonori Mimura; Takehide Satou, both of Katsuta, Japan

[73] Assignee: Hitachi, Ltd., Tokyo, Japan

[21] Appl. No.: 492,853

[22] Filed: Mar. 13, 1990

[30] Foreign Application Priority Data

Mar. 14, 1989 [JP] Japan .................. 1-061352

[51] Int. Cl.5 ........................................... G01N 35/02
[52] U.S. Cl. ................................. 422/67; 422/82.09; 436/50; 436/55; 356/73; 364/497
[58] Field of Search ............... 422/67, 82.09; 436/50, 436/55; 356/73; 364/497

[56] References Cited

U.S. PATENT DOCUMENTS

| 4,228,831 | 10/1980 | Kerns ........................ 73/864.12 |
| 4,263,512 | 4/1981 | Sagusa et al. ................ 250/373 |
| 4,451,433 | 5/1984 | Yamashita et al. ............ 422/63 |
| 4,472,505 | 9/1984 | Manabe et al. ............. 422/67 X |
| 4,612,289 | 9/1986 | Furuta et al. ................ 436/34 |
| 4,750,133 | 6/1988 | Eiskamp et al. ............. 364/497 |

FOREIGN PATENT DOCUMENTS

| 58-88663 | 5/1983 | Japan .................. 422/67 |
| 59-122954 | 7/1984 | Japan . |
| 61-137065 | 6/1986 | Japan .................. 364/497 |
| 61-218949 | 9/1986 | Japan .................. 422/67 |
| 61-262662 | 11/1986 | Japan . |
| 61-292540 | 12/1986 | Japan . |
| 62-98262 | 5/1987 | Japan . |
| 63-12964 | 1/1988 | Japan .................. 422/67 |
| 63-061959 | 3/1988 | Japan . |
| 63-206660 | 8/1988 | Japan .................. 422/67 |
| 63-281057 | 11/1988 | Japan . |

OTHER PUBLICATIONS

Hitachi Catalogue, Model 736 Series.

Primary Examiner—Robert J. Warden
Assistant Examiner—Stephanie Blythe
Attorney, Agent, or Firm—Fay, Sharpe, Beall, Fagan, Minnich & McKee

[57] ABSTRACT

An automatic analyzing apparatus and method transfers a sample to be examined to a sampling position, fractionally injects the sample into a reaction vessel by using sampling means, adds a reagent to the reaction vessel holding therein the sample fractionally injected to cause reaction, and measures absorbance of the reaction solution at predetermined time intervals using a photometer. A first check for checking whether an abnormality is present in the measurement result of each measurement item is made, followed by a second check for checking whether an abnormality is present on the basis of a change in the rate of absorbance measured after the reagent is added to the sample in the reaction vessel. Then, a third check computes correlation of measured absorbance data and checks whether an abnormality is present on the basis of the result of computation. Finally, a determination is made, with respect to the sample in accordance with an abnormal item when it is judged that an abnormality is present in the result of the first, second or third check, whether remeasurement is necessary, and for selecting, in case of remeasurement, either remeasurement under the same conditions or remeasurement with a reduced sample quantity as compared with that of the first measurement conditions. When remeasurement is determined, the sample is carried to the sampling position.

20 Claims, 5 Drawing Sheets

CHECKING ABSORBANCE CHANGE

AUTOMATIC ANALYZING APPARATUS AND METHOD FOR CLINICAL EXAMINATION

BACKGROUND OF THE INVENTION

1. Field of the Invention

The present invention relates to an automatic analyzing method and apparatus for clinical examinations, suitable for performing remeasurement with respect to a sample from which abnormal data have been detected.

2. Description of the Related Art

In conventional biochemical clinical examinations, there exist factors that cause data abnormality. For example, data abnormality is caused when a certain component of serum taken from a patent exists at an extremely high concentration; when a patient takes a large dose of medicine for medical treatment; when blood is fatty because of corpulence and hence the serum becomes abnormally lipemic; and when regular use of vitamin C (ascorbic acid) results in high concentration of vitamin C (ascorbic acid), and reaction of a medicine with the vitamin C causes false positivity.

If a report to a doctor is made from such a clinical examination room without notation of these data abnormalities, the doctor may make a mistake in diagnosis of the patient. In the case where a normal patient tests abnormal as a result of such a situation, no serious problem occurs because the doctor carries out a close examination. But when an examination for an abnormal patient indicates a false normal result due to such an inaccurate test, however, a disease may be overlooked, resulting in a medical mistake. Further, this might cause a mistake in judgment of medical treatment. In a clinical examination room, check methods such as those hereafter described have been adopted in order to uncover such mistakes that occur as a result of examination to improve the reliability of report data.

In biochemical clinical examinations, examinations of several to more than thirty items are generally carried out for each patient.

(1) Checking low value and high value

An upper limit value and a lower limit value are set for each item contained in a serum sample, for example. If these values are exceeded for a sample, the sample is diluted with a physiological solution of sodium chloride or a buffer solution and a remeasurement is taken. A clinical examination engineer (hereafter abbreviated to engineer) performs a data judgment and report. An example of abnormality whereby the upper limit value or the lower limit value is exceeded is shown in FIG. 1 of U.S. Pat. No. 4,263,512. For a normal sample, the absorbance curve is located at a low level. If there is turbidity in the sample, the absorbance curve often rises to an abnormally high level.

(2) Checking change in absorbance

If high activity of an enzyme contained in a serum is measured, a co-enzyme contained in the reagent is consumed in a short time. Therefore, there is adopted a method such as rate analysis, whereby a change in absorbance (hereafter abbreviated to $\Delta ABS$) is detected at fixed time intervals and the activity of the enzyme is measured on the basis of these changes. If the measurement is performed after a predetermined time has elapsed since injection of a reagent, however, the change rate of absorbance is measured in some cases after reaction with the reagent has been finished, and the absorbance changes little. In this case, erroneous measurement results are obtained.

That is to say, $\Delta ABS$ becomes large if the activity of the enzyme is high. If the activity of the enzyme is abnormally high, however, the substrate of the enzyme is rapidly consumed. When a predetermined time has elapsed, the reaction is substantially already finished. At this time, therefore, the measured value of $\Delta ABS$ becomes very small.

In measurement of an enzyme, therefore, a check line of upper limit or lower limit with respect to the measured value of absorbance is set as ABS·LIMIT. If the reaction becomes rapid because of abnormally high activity of the enzyme, and hence the absorbance ABS exceeds the above described check line ABS·LIMIT, an alarm indicating a data abnormality is generated for the sample by an automatic analyzing apparatus.

In case of turbidity, red color and yellow color of serum are measured after addition of a buffer solution to serum, and a data abnormality in the enzyme item and in the lipid item shows up in serum information containing the influence from muddiness caused by fat of serum, the influence from bilirubin and the influence from hemolysis.

(3) Data cross-check between items

When the function of the liver, kidney and the like is examined in a clinical examination, examination is performed not for one item but for several items. For example, in the examination of the liver function, GOT, GPT, LDH, ALP, $\gamma$-GTP and the like are examined. In case of patients having hepatitis, there is little possibility that only one item is abnormal and normal data are obtained in all other items. It is also unlikely that only one item is normal and all other items are abnormal. That is to say, a human body comprises various blood components that are mutually related and balanced. The engineer judges on the basis of these related data whether abnormalities in a certain item exist.

Some relations between these items are already known. Further, these relations are stored in a computer in the form of numerical formulas and used as a data check. Such a data crosscheck is disclosed in JJCLA (Japan Journal of Clinical Laboratory Automation), Japan Society for Clinical Laboratory Automation, Vol. 11, No. 5, 1986, pp. 58–62.

Conventionally, an engineer synthetically determines whether abnormalities exist by using these three kinds of representative data checking methods, and the engineer thus determines whether a readjustment should be made. Remeasurement may be made under the same condition as the condition of the first measurement or under a different condition. The engineer then compares the result of the remeasurement with the data obtained by the first measurement and judges which data should be reported to the doctor.

In the above described situations, three kinds of methods for determining whether data abnormalities exist are used separately. The engineer judges whether data are normal or not by watching these check results and determines whether a readjustment should be made or not. Problems of these methods will hereafter be described.

In the check of the upper limit value and the lower limit value described in (1), data of an item which should be originally abnormal become normal in some cases under the influence of another component contained in the serum. Because of the normality determination, the data of this item are not detected by this check. For checking these data abnormalities, turbidity and the like of the serum had to be checked in the check of absorbance change described in (2). Further, in the data cross-check between items described in (3), it was necessary to synthetically judge whether data were abnormal or not and whether reexamination was necessary or not on the basis of data of related items. Turbidity and hemolysis in serum, with resulting data abnormalities in some items, are difficult to determine in the data cross-check between items described in (3). It becomes possible, however, to detect the turbidity and hemolysis on the basis of absorbance level obtained after a reagent is added to serum by using the check of absorbance change rate described in (2).

At the present time, it is impossible to completely detect data abnormality by using, separately, any one of these three kinds of known methods. While watching results of these three kinds of check, the engineer makes a synthetic judgment and detects an abnormality. However, this synthetic judgment depends upon the experience of the engineer. Therefore, any judgment result varies with the engineer, and a person other than an expert may overlook a data abnormality. In a large hospital, the number of patients to be examined each day may be on the order of several hundred, and it is almost impossible for a person to carefully check data for all patients.

In general, samples judged to be abnormal are 5 to 10% of all samples. For an engineer to detect these few abnormal samples out of several hundred samples and request remeasurement of some items for each item is optimistic, and thus results in a problem.

In a system disclosed in JP-A-62-98262, an engineer performs a limit value check and a mutual check between items on the basis of various data obtained from the automatic analyzing apparatus, and reexamination is performed when an abnormal sample is found out.

On the other hand, in an automatic chemical analyzing apparatus disclosed in JP-A-61-262662, a value measured by the automatic chemical analyzing apparatus is compared with a reference value, and if the measured value exceeds the reference value, that sample is automatically transferred again to an examination station for reexamination of the sample.

SUMMARY OF THE INVENTION

An object of the present invention is to provide an automatic chemical analyzing apparatus and method for clinical examination that are capable of automatically detecting data abnormalities and taking remeasurements with respect to the abnormal samples, thus saving labor of examination engineers.

Another object of the present invention is to provide an automatic chemical analyzing apparatus and method which allow an engineer to set conditions for reexamination on the basis of contents of a detected data abnormality of an abnormal sample.

A further object of the present invention is to provide a mechanism for carrying an abnormal sample to an analyzing section for the purpose of reexamination when the abnormal sample has been discovered.

In accordance with an automatic analyzing method according to the present invention, an automatic analyzing apparatus for clinical examination including a measurement section for measuring absorbance of samples at preset time intervals, sample transfer means for transferring a sample between preset positions, and retransfer means for transferring a sample to the above described measurement section again, comprises a first check section for checking whether an abnormality based upon inadequate presetting in the analyzing apparatus with respect to a measurement object is present or not, a second check section for checking whether an abnormality is present or not on the basis of the rate of change of absorbance with respect to a measurement time, a third check section for computing correlations between measured data and checking whether an abnormality is present or not, and a data computation processing section for outputting information for each check section, whereby a determination as to whether remeasurement is necessary, and conditions for remeasurement, are determined, and for making the above described measurement section conduct a remeasurement of the sample.

The apparatus may be formed so that priority orders may be set among the first to third check sections, and check items of respective sections may be altered. Further, the apparatus may be formed so that priority orders may be set among check items of respective check sections.

Further, an automatic analyzing method according to the present invention comprises a first check step of checking whether an abnormality is present on the basis of an inadequate setting in an analyzing apparatus with respect to a measurement object, a second check step of checking whether an abnormality is present on the basis of the rate of change of absorbance with respect to a measurement of time, a third check step of checking whether an abnormality is present by computing correlations among measured data, a step of judging the necessity of remeasurement for each of the above described check steps, and a step of outputting measurement conditions for a remeasurement when remeasurement is necessary.

The first to third checks will now be described briefly.

(1) The first check
(Checking the low value and the high value of data)

An upper limit value and a lower limit value are set for each item of concern. Contents and/or degree of priority of reexamination processing to be performed when the limit value is exceeded are set.

(2) The second check
(Checking absorbance change)

For each item, a check time during the progress of reaction, a check scheme (absorbance or rate of change of absorbance), and contents and/or degree of priority of reexamination processing to be performed when the preset limit value is exceeded are set.

(3) The third check
(Data cross-check between items)

Data between items are checked by combining arithmetical operations and insertion of parentheses and coefficients, and limit values are set. For each of checked items, contents and/or degree of priority of reexamination processing to be performed when a limit value is exceeded are set.

After data checks described in (1) to (3) have been finished, degrees of priority of check results are compared for each item, and the engineer is informed of the contents of reexamination processing that have the highest degree of priority.

The engineer may consider priority relationships in accordance with the engineer's own determination, and specify degrees of priority of respective checks accordingly. It then becomes possible to automatically check a data abnormality and execute instead the synthetic check which has been performed by the engineer.

After the synthetic check, a sample which has been judged to require a remeasurement is automatically extracted by the automatic analyzing apparatus and transferred to the analyzing section. At this time, a directive concerning the processing contents of remeasurement is also sent to the analyzing section. As a result, the sample which has been judged by the data computation processing section to require a remeasurement automatically undergoes remeasurement in the analyzing section, eliminating the need for further efforts on the part of the engineer.

DETAILED DESCRIPTION OF THE PREFERRED EMBODIMENTS

Figure 1:
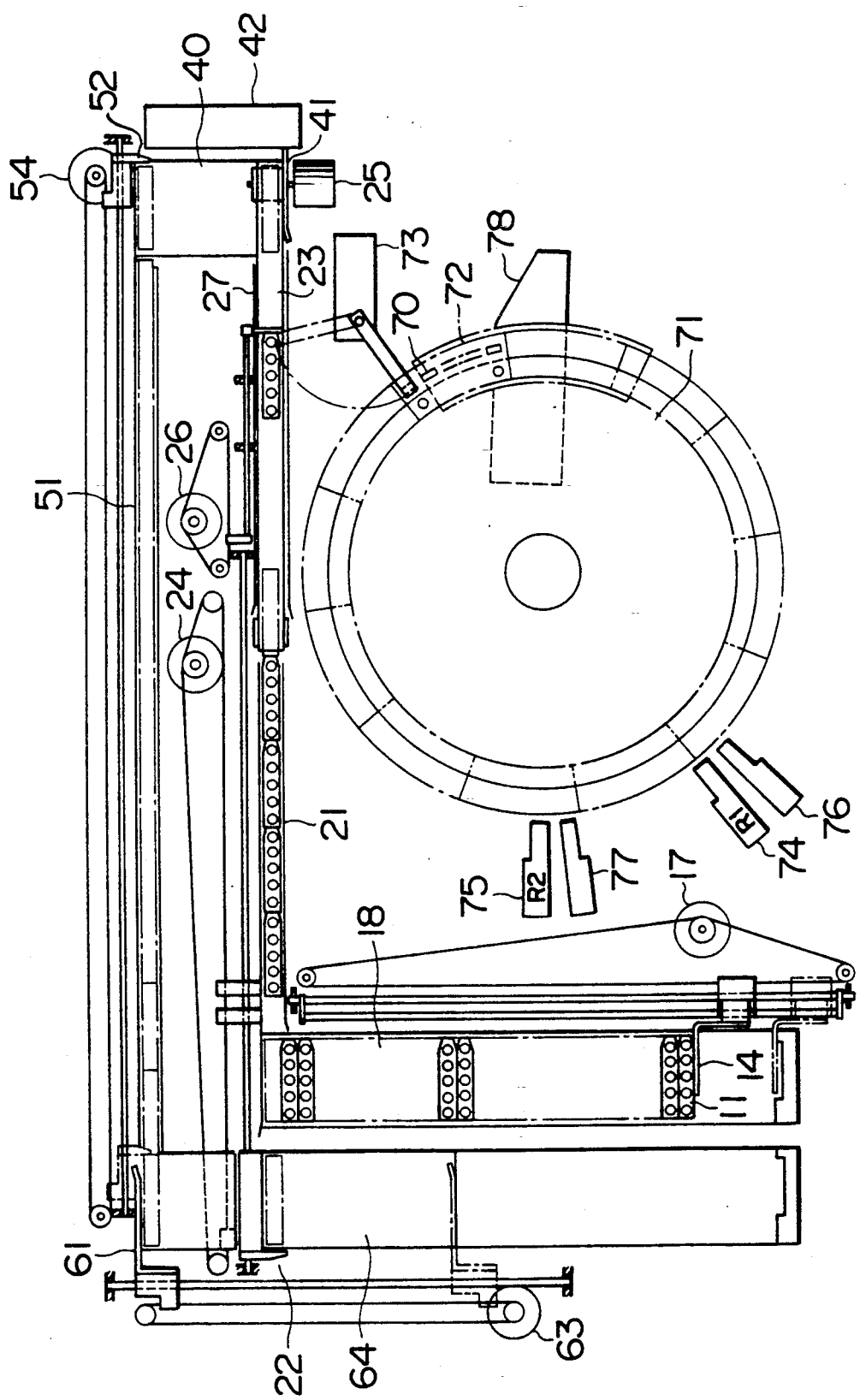
FIG. 1 is a configuration diagram showing an embodiment of the present invention.

An embodiment of the present invention will hereafter be described by referring to the drawings.

In FIG. 1, each of the sample racks 11 placed on a line 18 of the analyzing apparatus houses five samples. A leading sample rack is pushed out onto a line 21 by an arm 14 driven by a motor 17. Further, the sample rack 11 is transferred toward another line 23 by an arm 22 driven by a motor 24. The line 23 comprises a belt driven by a motor 25. The sample rack 11 is transferred to the right by that belt and stopped at a predetermined sampling position by a stopper 27 which is positioned by a motor 26. Owing to the function of this stopper, samples housed in the sample rack 11 are successively sampled one by one by a sampler 72, and the sampled portions injected into reaction vessels 70 on a turntable 71. When sampling of all samples on the sample rack 11 has been finished, the sample rack 11 is transferred to the right end of the line 23, transferred onto a line 51 by an arm 41, which is moved by drive means 42, and further transferred on the line 51 to the left end by an arm 52 driven by a motor 54. Up to nine sample racks are held on the line 51 and wait on the line 51 until the analysis results of samples held on each sample rack are outputted.

When analysis results are outputted from the analyzing section and it is judged that all of the five samples housed in the leading sample rack 11 are normal, that sample rack is transferred onto a line 64 over the line 21 by an arm 61 driven by a motor 63. When one sample housed in a sample rack is judged to be abnormal, that sample rack is stopped on the line 21 and then transferred to the sampling position again by the arm 22. By the same procedure as that described before, sampling is again performed. However, a sample which has already undergone one reexamination (a second examination) is not subject to a third examination.

The series of operations heretofore described is executed until all sample racks 11 on the line 18 are sent out and sent into the line 64.

The turntable 71 is rotated by 360° plus the angle corresponding to one reaction vessel 70 each time sampling and injection into each reaction vessel 70 are performed. Each time the turntable 71 completes one revolution, therefore, all reaction vessels 70 are passed through a photometry section 78 to undergo photometry. On the turntable, 50 reaction vessels are disposed on a circumference. If the turntable completes one revolution, therefore, reaction vessels 70 are advanced by a distance corresponding to one reaction vessel. Eventually, each reaction vessel 70 passes through the photometry section 78 fifty times and photometry is performed fifty times until that reaction vessel is stopped again at the same position as the start point. The position where each reaction vessel 70 passes through the photometry section 78 is referred to as the measuring point. This measuring point can be represented by the number of times the reaction vessel passes through the photometry position since sample injection. Rotation of the turntable is executed at intervals of 12 seconds. Since there are 50 reaction vessels, measurements can be taken for one sample up to a maximum of 10 minutes. Numerals 76 and 77 denote positions where first and second reagents are injected, respectively. Numerals 76 and 77 denote agitation sections, and numeral 72 denotes a washing section. The turntable operation, sampling, reagent injection, photometry and washing heretofore described are performed by using generally known methods as shown in "Model 736 Series", a catalog of Hitachi, Ltd.

Figure 2:
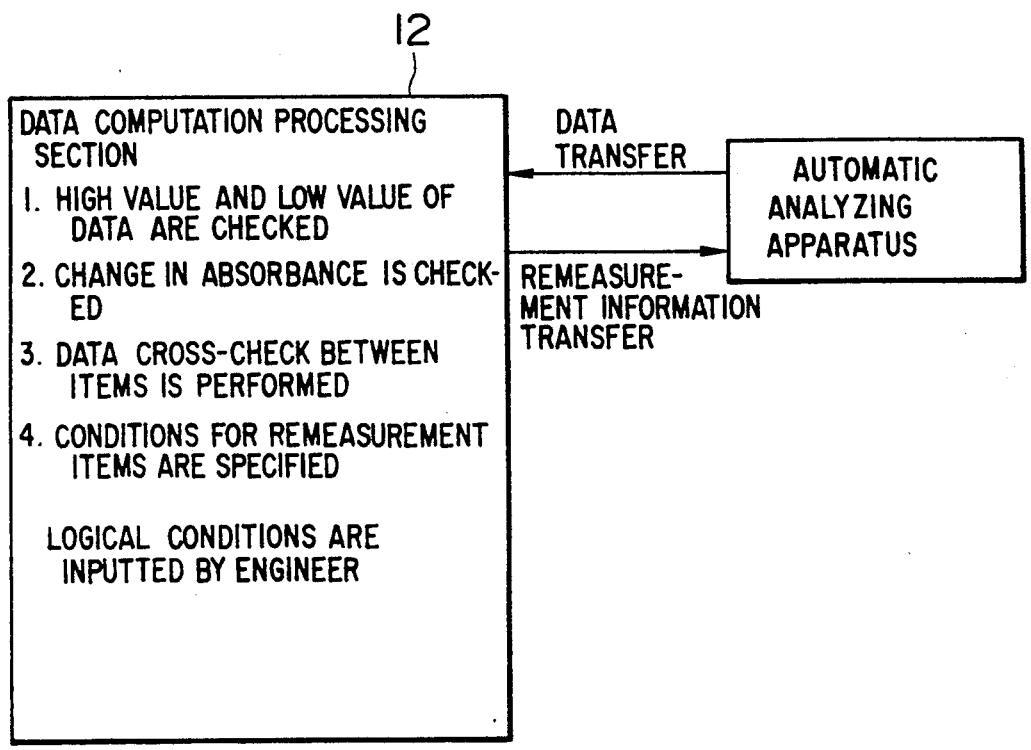
FIG. 2 is a diagram showing data transmission between an automatic analyzing apparatus and a data computation processing section.

The sample rack 11 waits for the output of data at a data output waiting position (the left end of the line 51). When data are outputted, the data are transmitted from the automatic analyzing apparatus to a data computation processing section 12 (FIG. 2), where it is judged whether an abnormality is present or not.

Figure 3:
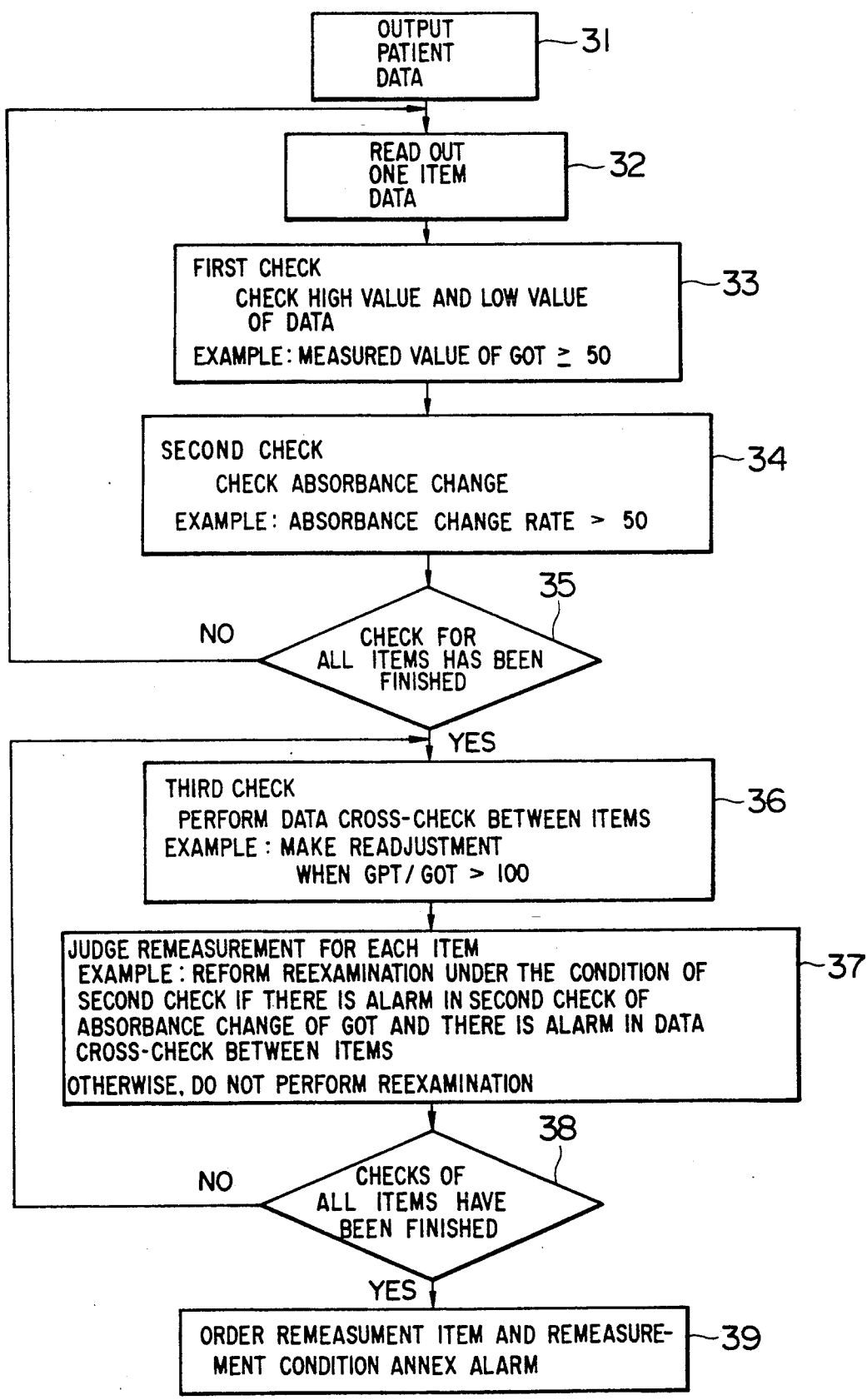
FIG. 3 is a flow diagram of data abnormality check according to the present invention.

In the data computation processing section 12, data obtained form respective samples are checked in accordance with a flow chart shown in FIG. 3.

With reference to FIG. 3, data of one patient are outputted at step 31, and data of one examination are read out at step 32. A first check is performed at step 33. This first check comprises an alarm check relating to the apparatus status in addition to the above described check of the high value and low value. Checks having results as shown in Table 1 are performed.

TABLE 1

| Degree of Priority | Kind of abnormality | Procedure taken |
|---|---|---|
| 1 | Insufficient samples Abnormality in A-D converter Insufficient reagents | Remeasurement is not made |
| 2 | ABS.LIMIT of absorbance is exceeded Measurement range is exceeded (upper limit value) Immunity antigen is exceeded (Prozone limit) | Remeasurement is made with a sample quantity less than that of the first measurement (Sample quantity is specified for each item) |
| 3 | Enzyme reaction curves Cell blank is abnormal Measurement range is exceeded | Remeasurement is made under the same analysis conditions as for the first measurement |

TABLE 1-continued

| | Degree of Priority | Kind of abnormality | Procedure taken |
|---|---|---|---|
| | | (lower limit value) | |

With reference to Table 1, remeasurement cannot be made in the case of insufficient samples, abnormality in the A-D converter and insufficient reagents. As the cited procedure, therefore, remeasurement is not made. Insufficient samples and insufficient reagents can be detected by liquid surface sensors such as are respectively disclosed in U.S. Pat. No. 4,228,831 and 4,451,433, for example.

Abnormalities of exceed the ABS·LIMIT of absorbance, the upper limit value of the measurement range and the limit of immunity antigen are caused by the fact that the enzyme activity is too high and, hence, the progress of reaction is too fast. Therefore, a measurement is made with a reduced sample quantity.

"Enzyme reaction curves" indicates the fact that the reaction curve largely deviates from the normal curve by some cause. "Cell blank is abnormal" indicates that an error is caused in the measured value because of dirt or the like on the reaction tube. "Measurement range is exceeded (lower limit value)" indicates that the reaction is abnormally slow. In these cases, remeasurement is made under the same conditions as that of the first time in order to reaffirm the measured value.

Depending upon the kind of abnormality which has occurred, degree of priority is given to procedures to be executed as indicated in the left column of Table 1. In case an alarm of insufficient samples is generated, for example, remeasurement is not conducted as the disposition. In case alarms of "insufficient samples" and "ABS LIMIT is exceeded" are simultaneously generated, remeasurement is not conducted in accordance with the procedure listed for "insufficient samples" having higher degree of priority. The first check for one measurement item is thus finished.

A second check relating to the absorbance change is then performed at step 34. In the second check, difference in absorbance, rate of change of absorbance and absorbance measuring point are specified, and arithmetic operations, parentheses and coefficients are set for each item as shown in Table 2. Check formulas are made, and whether reexamination should be performed and the reexamination conditions are determined in accordance with the check formulas.

TABLE 2

| Item | Measuring point | Check formula | Procedure taken |
|---|---|---|---|
| GOT | $A_5, A_6$ | $\dfrac{A_5 + A_6}{2} \leqq 8000$ | Reexamination is not performed. |
| GPT | " | " | |
| LDH | $A_5$ to $A_{12}$ | $\Delta A_{5 \text{ to } 12} \geqq 50$ (Change rate of absorbance) | Reexamination with reduced quantity of samples |
| BUN | $A_{15}, A_{16}, A_{26}, A_{27}$ | $\dfrac{A_{15} + A_{16}}{2} - \dfrac{A_{26} + A_{27}}{2} \geqq 500$ | Reexamination with reduced quantity of samples |
| AMY | $A_3, A_4, A_{15}, A_{16}$ | $\dfrac{A_3 + A_4}{2} - \dfrac{A_{15} + A_{16}}{2} \geqq 500$ | Reexamination with reduced quantity of samples |
| ALP | $A_5, A_6$ | $\dfrac{A_5 + A_6}{2} \geqq 5000$ | Reexamination with the same sample quantity as for that of the measurement |

Figure 4:
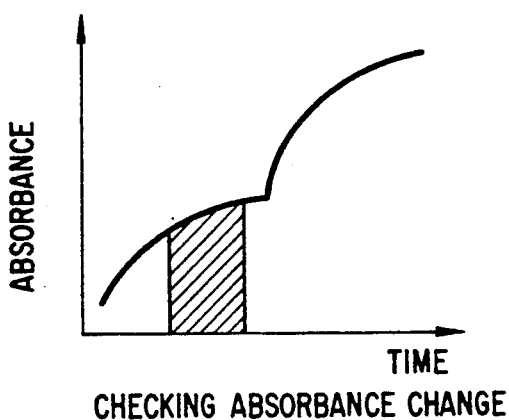
FIG. 4 is a diagram for illustrating an example of an absorbance change according to the present invention.

FIG. 4 shows a graph representing absorbance change over time. The shaded region indicates the measurement range, and a discontinuous point between curves indicate the injection point of the second reagent.

Respective items of Table 2 will hereafter be described.

(1) GOT check:

After the first reagent has been added, absorbance is measured at intervals of fixed time (for example, at intervals of 12 seconds). Immediately after the first reagent is added, data contain many errors because bubbles are generated by addition of the reagent and the temperature of the reagent does not become constant. Therefore, the measuring points are not used as a check. Immediately before addition of the second reagent when 4 to 5 minutes have elapsed, a side reaction represented by the following formula occurs and a reagent NADH is consumed, absorbance of NADH thus reaching a low level:

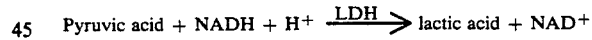

Pyruvic acid + NADH + H$^+$ $\xrightarrow{\text{LDH}}$ lactic acid + NAD$^+$

Pyruvic acid and LDH are contained in the sample.

Even if absorbance is measured at measuring points 20 to 25 when 4 to 5 minutes have elapsed, the quantity of NADH contained in the reagent cannot be accurately measured because of this side reaction. Further, if absorbance is measured only once, there is a fear that the measurement is affected by electrical noise in the amplifier. Therefore, more accurate result can be obtained by averaging two measurements. Therefore, the mean value of measured values $A_5$ and $A_6$ respectively obtained at measuring points 5 and 6 is calculated as shown in Table 2. In the check formula, "8000" at the check point is obtained by multiplying absorbance by 10,000 and represents an absorbance of 0.8. In general, each of the reagents used for measuring GOT and GPT has an absorbance nearly equal to 1.2. On the other hand, absorbance of each of these reagents naturally decreases by approximately 0.2 in one week. If absorbance becomes too small, measurement becomes impossible. Accordingly, its limit point, absorbance of 0.8, i.e., 8000 has been specified.

(2) GPT check:

In the same way as GOT, GPT is one kind of amino acid transition enzyme. Since its analysis method is also based upon the same principle as that of GOT, the same check method is used. (3) LDH check:

The first reagent is added. After the temperature becomes constant and bubbles disappear, the change rate of absorbance of the reaction liquid is measured at measuring point 5 and thereafter. As the first reagent, an NADH aqueous solution is used. As the second reagent, a pyruvic acid water solution is used. Its side reaction is represented by the following formula:

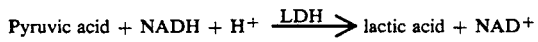

If the reaction vessel is tainted by enzyme reacting with NADH when the first reagent is added, NADH contained in the reagent is consumed and absorbance is at its low level. For this check, therefore, the change rate of absorbance at measuring points 5 to 21 is calculated by using the method of least square.

(4) BUN check:

Measurement of BUN is performed for quantitating urea contained in serum. This quantitating method can be represented by the following formula:

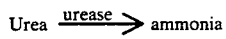

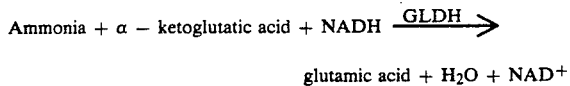

In this method, urea is resolved and ammonia is quantitated. If the serum is left as it is, protein contained in the serum is resolved by micro-organisms and hence ammonia is unfavorably increased in some cases. If the absorbance obtained immediately after addition of the second reagent largely changes from the absorbance obtained before addition, then a large quantity of ammonia is present in the serum. Therefore, the difference between the value measured at measuring points 15 and 16 before addition of the second reagent and the value measured at measuring points 26 and 27 immediately after addition of the second reagent is calculated. When the difference is larger than 500, ammonia is judged to be excessive.

(5) AMY check:

AMY is an enzyme for resolving sugar. In sera of some patients, a large quantity of sugar is contained. The reagent for AMY measurement contains a fixed quantity of sugar, which is resolved by the action of AMY. The reagent reacts with components resulting from the resolution. On the basis of the rate of reaction at this point, the activity value of AMY is measured. If a large quantity of sugar is contained in serum, absorbance rapidly changes after addition of the first reagent. Further, because there are components directly reacting with the reagent and components which first resolve and then react with the reagent, this reaction does not proceed at a fixed rate. Therefore, abnormality is judged to be present if the difference between the value measured at the measuring points 3 and 4 soon after the addition of the first reagent and the value measured at the measuring points 15 and 16 after the elapse of approximately 2 minutes is larger than 500.

(6) ALP check:

For ALP, a measuring wavelength of 415 nm is used. In some cases, however, data rapidly become high values after addition of the first reagent under the influence of hemoglobin and bilirubin contained in serum. In particular, bilirubin becomes large in absorbance immediately after the addition of the first reagent. Therefore, measurement is taken at measuring points 5 and 6 where the temperature becomes constant and generation of bubbles finishes soon after the addition of the first reagent.

If steps 33 and 34 are finished for one item as heretofore described, it is checked at step 35 whether a check has been finished for all measurement items or not. If the judgment at step 35 is "NO", processing returns to step 32, where data of the next item are read out and the first check and the second check are performed in the same way as the foregoing description. If checks of all items have been judged finished at step 35, a third check is performed at step 36 and the remeasurement condition is determined in accordance with the condition of the check result having a higher degree of priority at step 37. At step 38, it is judged whether checks of all items included in the third check have been finished or not. At step 39, the remeasurement condition based upon step 37 is ordered.

In the third check, data cross-check between items is performed. The third check comprises the steps of adding coefficients to data of respective items, entering parentheses to form formulas, performing arithmetic operations, and comparing the result of operations with a predetermined limit value. FIGS. 5A to 5E show data check rules between items. Checks based upon these five rules are executed in order complying with priority orders described later.

Figure 5A:
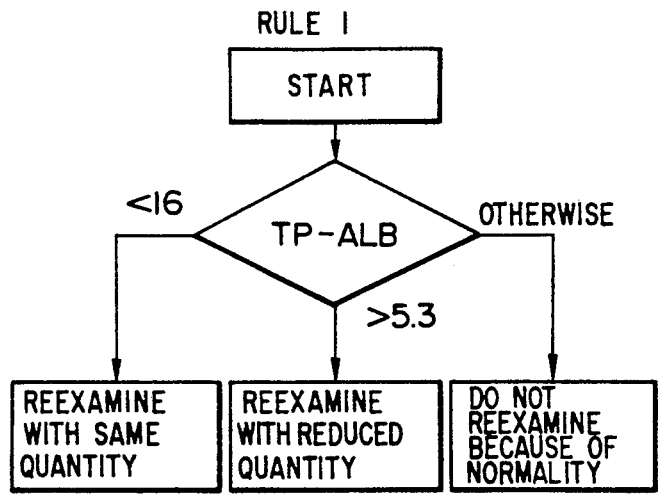
FIGS. 5A to 5E are flow charts showing examples of a check rule of a third check according to the present invention.

In rule 1 shown in FIG. 5A, the relationship between TP and ALB is checked. In general, the difference between TP and ALB is globulin. It is known that the quantity of globulin falls within a nearly fixed region If the difference is too large or too small, reexamination is specified.

Figure 5B:
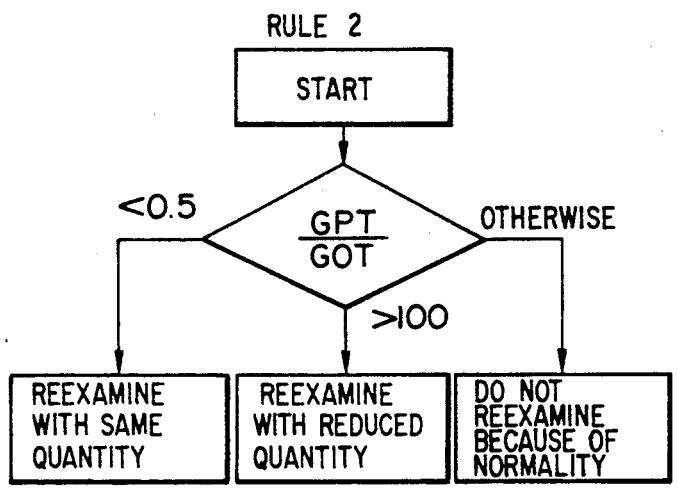

In rule 2 shown in FIG. 5B, the relationship between GOT and GPT is checked. In general, the ratio between them is constant. When the ratio is outside the normal region, reexamination is ordered.

Figure 5C:
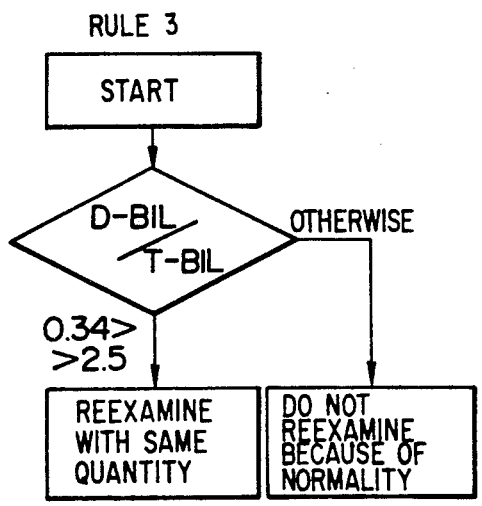

In rule 3 shown in FIG. 5C, bilirubin (T-BIL and D-BIL) of a part of the examination of the liver is checked. It is known that one of T-BIL and D-BIL also increases if the other of them increases and one of them also decreases if the other of them decreases. Therefore, the check is performed by checking whether the ratio between them is within a fixed range or not.

Figure 5D:
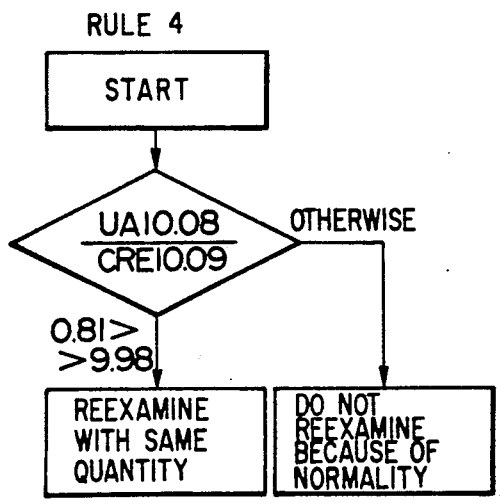

In rule 4 shown in FIG. 5D, the relationship between UA and CRE in the examination of kidney performance is checked. In the same way as the case of bilirubin, this is checked in the form of the ratio between them.

Figure 5E:
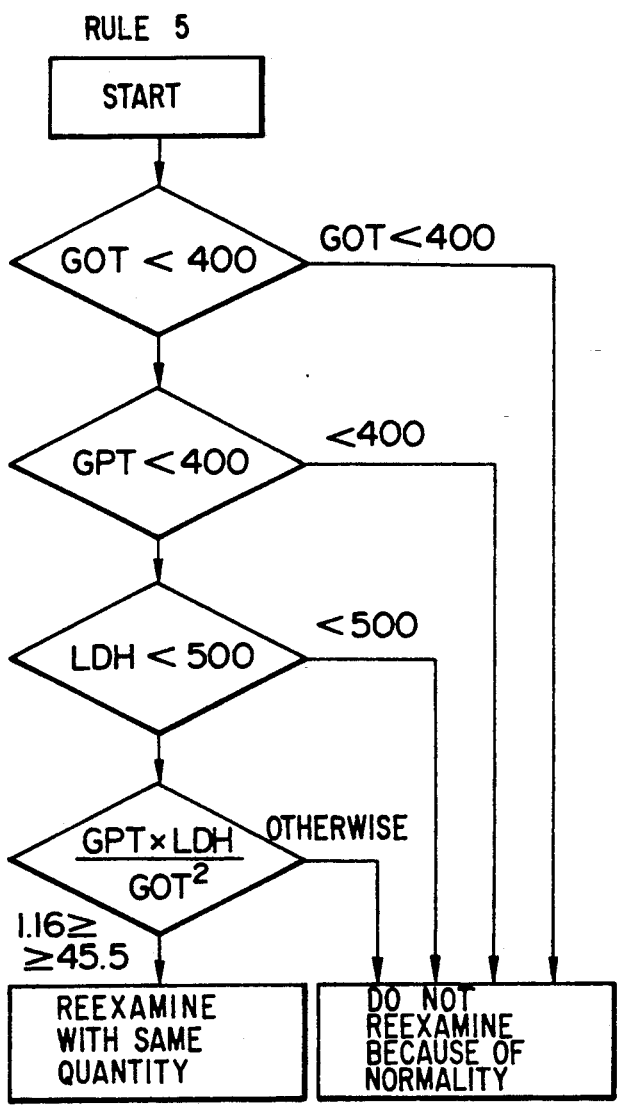

In rule 5 shown in FIG. 5E, liver performance is checked to see whether an abnormality is present or not.

Figure 6:
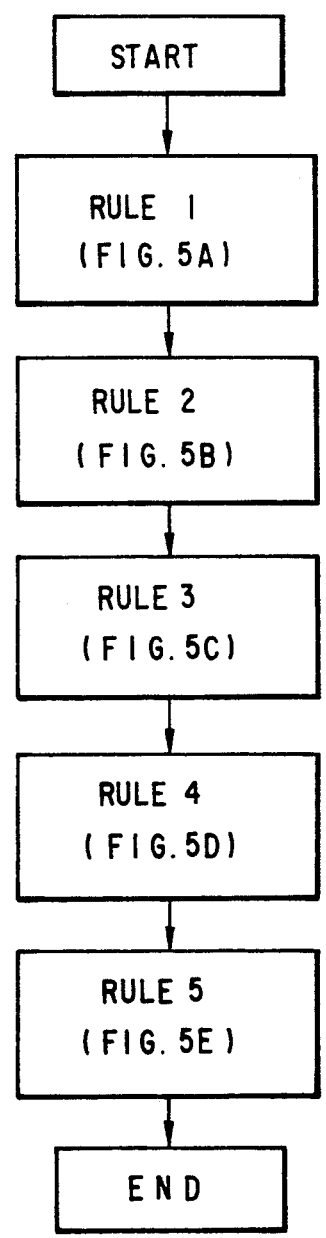
FIG. 6 is a flow chart obtained when degrees of priority are assigned to the rules shown in FIGS. 5A to 5E.

In inter-head checks in the third check, orders of priority are given in order by rule number. It is now assumed that an abnormality is judged to be present and reexamination is ordered in a certain item by a certain rule, and reexamination is ordered with respect to that item by a different rule as well. If the contents of reexamination are different at that time and reexamination is executed with the identical or reduced quantity of samples, contents of the smaller rule number having a higher priority degree are ordered. If one rule orders reexamination and another rule does not order reexamination, however, reexamination is executed. With respect to GOT, for example, reexamination can be ordered by the rule 2 and the rule 5. In this case, however, the rule 2 takes priority. As shown in FIG. 6, therefore, FIG. 5A to 5E may be executed one after another.

By these three kinds of checks, reexamination contents are ordered, respectively. These checks are provided with degrees of priority in the following order (step 37):

1. The first check (check on apparatus state)
2. The second check (check on absorbance change)
3. The third check (check between items)

If the reexamination for a certain item is requested at two places, i.e., the second check section and the third check section, reanalysis is performed under the reexamination condition of the second check section having a higher degree of priority. If a reexamination request is issued at at least one check section, reaxamination is executed.

After completion of the check, the sample rack 11 which has been located at a data output waiting position 51 is housed in the line 64 unless a reexamination request for a sample on the rack is present. If a reexamination request is present, the sample rack 11 is transferred to the analysis section again via the line 21 and analyzed.

In the present embodiment, an abnormal sample is automatically checked and picked up, and request item specification of remeasurement and remeasurement are automatically made, resulting in automation and labor saving in the examination room.

The present invention makes it possible to synthetically judge and find out abnormalities in data at all times without recourse to the engineer's experience. Further, a large number of samples can also be processed in real time. As compared with the case where the engineer personally checks and judges, labor can be largely saved. Further, since the apparatus automatically takes a remeasurement on samples, there is no fear that the examination engineer takes a wrong sample. The reliability of examination is thus improved.

We claim:

1. An automatic analyzing apparatus for clinical examination, comprising:

sampling means for transferring a sample to be examined to a sampling position and for fractionally injecting the sample into a plurality of reaction vessels, said sample containing at least one measurement item;

means for adding a reagent to the reaction vessels holding therein the sample fractionally injected by said sampling means to create a reaction solution in each reaction vessel;

means for measuring measurement item absorbance of each reaction solvent at predetermined time intervals;

first check means for checking whether an abnormality is present in the absorbance value of each measurement then;

second check means for checking whether an abnormality is present on the basis of the rate of change of each said absorbance value measured by said measurement means after the reagent is added to the sample in each said reaction vessel;

third check means for computing a correlation between data obtained on the basis of absorbance values of measured items measured by said measurement means, and for checking whether an abnormality is present on the basis of the correlation computation; and means for determining, with respect to said sample in accordance with an abnormal measurement item when it is judged than an abnormality is present in the result of at least one check performed by said first, second and third check means, whether remeasurement is necessary and for selecting, in case of remeasurement, remeasurement conditions selected from the group consisting of remeasurement under the same conditions and remeasurement with a diluted sample as compared with that of the first measurement; said means for determining comprising means for presetting degrees of priority of said first, second and third check means; and means for determining, when abnormalities are sensed in a plurality of check results by at least one of said first, second and third check means, whether remeasurement is necessary and the remeasurement conditions in case of remeasurement, in accordance with the result of an abnormality based upon a check having the highest degree of priority, among all checks that show an abnormality, wherein said priority degree presetting means comprises means for presetting the degree of priority in order of said first check means, said second check means and said third check means.

2. An automatic analyzing apparatus for clinical examination according to claim 1, wherein said priority degree presetting means further comprises means for giving priority orders to respective check items of said first, second and third check means.

3. An automatic analyzing apparatus for clinical examination according to claim 1, wherein said first check means comprises means for checking a measurement item which cannot be remeasured.

4. An automatic analyzing apparatus for clinical examination according to claim 1, wherein said first check means comprises means for detecting that an absorbance value measured by said measurement means exceeds a range defined by predetermined upper limit and lower limit values.

5. An automatic analyzing method for clinical examination comprising:

a sampling step for transferring a sample containing at least one measurement item to be examined to a sampling position and for fractionally injecting the sample into a plurality of reaction vessels;

a measurement step for adding a reagent to each reaction vessel holding therein a sample fractionally injected at said sampling step to create a reaction solution, and for measuring measurement item absorbance of each reaction solution at predetermined time intervals;

a first check step for checking whether an abnormality is present in the absorbance value of each measurement item;

a second check step for checking whether an abnormality is present on the basis of the rate of change of each said absorbance value measured at said measurement step after the reagent is added to the sample in each said reaction vessel;

a third check step for computing a correlation between data obtained on the basis of absorbance values of measurement items measured at said measurement step, and for checking whether an abnormality is present on the basis of the correlation computation; and a step for determining, with respect to said sample in accordance with an abnormal measurement item when it is judged than an abnormality is present in the result of at least one check performed at said first, second and third check steps, whether remeasurement is necessary and for selecting, in case of remeasurement, one of remeasurement under the same conditions and remeasurement with a diluted sample as compared with that of the first measurement.

6. An automatic analyzing apparatus for clinical examination, comprising:

sampling means for transferring a sample to be examined to a sampling position and for fractionally injecting the sample into a plurality of reaction vessels, said sample containing at least one measurement item;

means for adding a reagent to the reaction vessels holding therein the sample fractionally injected by said sampling means to create a reaction solution in each reaction vessel;

means for measuring measurement item absorbance of each reaction solution at predetermined time intervals;

first check means for checking whether an abnormality is present in the absorbance value of each measurement item;

second check means for checking whether an abnormality is present on the basis of the rate of change of each said absorbance value measured by said measurement means after the reagent is added to the sample in each said reaction vessel;

third check means for computing a correlation between data obtained on the basis of absorbance values of measured items measured by said measurement means, and for checking whether an abnormality is present on the basis of the correlation computation;

means for holding the sample in waiting state at a predetermined position until checks are completed by said first, second and third check means;

means for determining, with respect to said sample in accordance with an abnormal measurement item when it is judged than an abnormality is present in the result of at least one check performed by said first, second and third check means, whether remeasurement is necessary and for selecting, in case of remeasurement, one of remeasurement under the same conditions and remeasurement with a diluted sample as compared with that of the first measurement; and means for sending, when a check result is judged normal by one of said first, second and third check means, the sample containing the measurement item judged normal to a discharge position and for carrying, when remeasurement is determined by said determining means, said sample to said sampling means for remeasurement.

7. An automatic analyzing method for clinical examination, comprising:

a sampling step for transferring a sample containing at least one measurement item to be examined to a sampling position and for fractionally injecting the sample into a plurality of reaction vessels;

a measurement step for adding a reagent to each reaction vessel holding therein a sample fractionally injected at said sampling step to create a reaction solution, and for measuring measurement item absorbance of each reaction solution at predetermined time intervals;

a first check step for checking whether an abnormality is present in the absorbance value of each measurement item;

a second check step for checking whether an abnormality is present on the basis of the rate of change of each said absorbance value measured at said measurement step after the reagent is added to the sample in each said reaction vessel;

a third check step for computing a correlation between data obtained on the basis of absorbance values of measurement items measured at said measurement step, and for checking whether an abnormality is present on the basis of the correlation computation;

a step for holding the sample in waiting state at a predetermined position until said first, second and third steps are completed;

a step for determining, with respect to said sample in accordance with an abnormal measurement item when it is judged than an abnormality is present in the result of at least one check performed at said first, second and third check steps, whether remeasurement is necessary and for selecting, in case of remeasurement, one of remeasurement under the same conditions and remeasurement with a diluted sample as compared with that of the first measurement; and a step for sending, when the check result is judged normal at one of said first, second and third check steps, said sample to a discharge position and for carrying, when remeasurement is determined at said determining step, said sample to said sampling position for remeasurement.

8. An automatic analyzing apparatus as claimed in claim 1, further comprising means for carrying, when remeasurement is determined by said determining means, said sample to said sample means for remeasurement.

9. An automatic analyzing method for clinical examination as claimed in claim 5, further comprising a step for carrying, when remeasurement is determined at said determining step, said sample to said sampling position for remeasurement.

10. An automatic analyzing apparatus for determining whether remeasurement of absorbance values of one or more measurement items of a sample that has previously been measured is necessary, comprising:

first check means for checking whether an abnormality is present in absorbance values previously determined for measurement items whose absorbance values were previously measured;

second check means for checking whether an abnormality is present on the basis of the rate of change of each said absorbance value measured previously;

third check means for computing a correlation between data obtained on the basis of absorbance values of measurement items previously measured, and for checking whether an abnormality is present on the basis of the correlation computation; and means for determining, with respect to said sample in accordance with an abnormal measurement item when it is judged that an abnormality is present in the result of at least one check performed by said first, second and third check means, whether remeasurement is necessary and for selecting, in case of remeasurement, one of remeasurement under the same conditions and remeasurement with a diluted sample as compared with that of the previous measurement.

11. An automatic analyzing apparatus as claimed in claim 10, wherein said determining means comprises:
means for presetting degrees of priority of said first, second and third check means; and
means for determining, when abnormalities are sensed in a plurality of check results by said first, second and third check means, whether remeasurement is necessary and remeasurement conditions in case of remeasurement, in accordance with the result of an abnormality based upon a check having the highest degree of priority among all checks that show an abnormality.

12. An automatic analyzing apparatus as claimed in claim 13, wherein said priority degree presetting means comprises means for presetting the degree of priority in order of said first check means, said second check means and said third check means.

13. An automatic analyzing apparatus as claimed in claim 10, wherein said first check means comprises means for detecting that a previously-measured absorbance value exceeds a range defined by predetermined upper limit and lower limit values.

14. An automatic analyzing apparatus as claimed in claim 10, further comprising means for sending, when a check result is judged normal by one of said first, second and third check means, the sample containing the measurement item judged normal to a discharge position and for carrying, when remeasurement is determined by said determining means, said sample to a sampling position for remeasurement.

15. An automatic analyzing apparatus as claimed in claim 1, further comprising means for establishing degrees of priority among abnormalities determined by said first check means, and for indicating the order of remeasurement pursuant to the abnormalities determined by said first check means in accordance with the established degrees of priority.

16. An automatic analyzing apparatus as claimed in claim 10, further comprising means for establishing degrees of priority among abnormalities determined by said first check means, and for indicating the order of remeasurement pursuant to the abnormalities determined by said first check means in accordance with the established degrees of priority.

17. An automatic analyzing apparatus as claimed in claim 1, further comprising means for establishing degrees of priority among abnormalities determined by said second check means, and for indicating the order to remeasurement pursuant to the abnormalities determined by said second check means in accordance with the established degrees of priority.

18. An automatic analyzing apparatus as claimed in claim 10, further comprising means for establishing degrees of priority among abnormalities determined by said second check means, and for indicating the order or remeasurement pursuant to the abnormalities determined by said second check means in accordance with the established degrees of priority.

19. An automatic analyzing apparatus as claimed in claim 1, further comprising means for establishing degrees of priority among abnormalities determined by said third check means, and for indicating the order to remeasurement pursuant to the abnormalities determined by said third check means in accordance with the established degrees of priority.

20. An automatic analyzing apparatus as claimed in claim 10, further comprising means for establishing degrees of priority among abnormalities determined by said third check means, and for indicating the order of remeasurement pursuant to the abnormalities determined by said third check means in accordance with the established degrees of priority.

* * * * *